United States Patent [19]

Semler et al.

[11] 3,962,326

[45] June 8, 1976

[54] PROCESS FOR THE MANUFACTURE OF CARBOXYLIC ACID CHLORIDES

[75] Inventors: Günther Semler, Kelkheim, Taunus; Georg Schaeffer, Hofheim, Taunus; Karl Waldmann, Neuenhain, Taunus, all of Germany

[73] Assignee: Hoechst Aktiengesellschaft, Frankfurt am Main, Germany

[22] Filed: Apr. 24, 1974

[21] Appl. No.: 463,826

[30] Foreign Application Priority Data

Apr. 26, 1973 Germany............................ 2321122

[52] U.S. Cl. ........................................... 260/544 K
[51] Int. Cl.² ........................................... C07C 51/58
[58] Field of Search ........ 260/544 K, 544 M, 544 D

[56] References Cited

UNITED STATES PATENTS

| | | | |
|---|---|---|---|
| 3,184,506 | 5/1965 | Parker et al..................... | 260/544 L |
| 3,318,950 | 5/1967 | Christoph et al. .............. | 260/544 K |
| 3,673,247 | 6/1972 | Hill et al. ........................ | 260/543 R |

FOREIGN PATENTS OR APPLICATIONS

| | | | |
|---|---|---|---|
| 401,643 | 2/1932 | United Kingdom............ | 260/544 M |

OTHER PUBLICATIONS

Fieser et al., "Organic Chemistry," Reinhold Publishing Corp. (1956) p. 589.

Mar., "Advanced Organic Chemistry", McGraw–Hill N.Y. (1968) pp. 325, 319, 320, 335, 778.

Mar., "Advanced Organic Chemistry", McGraw–Hill N.Y. (1968) pp. 346, 374.

*Primary Examiner*—John F. Terapane
*Attorney, Agent, or Firm*—Curtis, Morris & Safford

[57] ABSTRACT

Process for preparing carboxylic acid chlorides by reaction of carboxylic acids or carboxylic anhydrides with phosgene at temperatures of from 0° to 180°C in the presence of a catalyst, wherein 0.01 to 10 weight percent, calculated on the carboxylic acid or the carboxylic anhydride, of trisubstituted phosphine oxides or trisubstituted phosphine sulfides or reaction products of these compounds with phosgene and/or acids or acid anhydrides or mixtures of these compounds are used as catalyst.

7 Claims, No Drawings

PROCESS FOR THE MANUFACTURE OF CARBOXYLIC ACID CHLORIDES

The manufacture of carboxylic acid chlorides by reacting carboxylic acids with phosgene is well known to the art. Pressure or catalysts are necessary for completing this reaction.

According to French Patent no. 1,226,245 there are used as phosgenation catalysts dimethyl-formamide or, generally, N,N-dialkyl-carbonamides. However, these catalysts present the inconvenience that, towards the end of the reaction, they cause resin formation which results in an often strong coloration of the final products. The increasingly heavy contamination of the reactants practically forbids a continuously operated reaction.

According to U.S. Pat. No. 3,184,506 and German "Offenlegungsschrift" No. 2,057,956 this formation of resin which occurs towards the end of the reaction only is prevented by operating always in the presence of free acid, i.e. the reaction is not carried through to the end. This processing method presents the inconvenience that it requires additionally an often complicated separation of the acid chlorides formed from the non-reacted acid.

According to German Patent nos. 1,668,276 and 1,668,277 less colored products are obtained when quaternary ammonium salts or phosphonium salts or tetramethyl-thio-urea are used as phosgenation catalysts. These catalysts present especially the inconvenience that they are inapt for the phosgenation of numerous acids so that their application is limited, and furthermore said catalysts have to be used in relatively large quantities. Besides, the reaction speeds and yields obtainable — especially as far as the aromatic range is concerned — are very low and not fit for technological processes.

It has now been found that carboxylic acids or carboxylic acid anhydrides can be reacted with phosgene at temperatures from 0 to 180°C rapidly and with good yields to produce very pure carboxylic acid chlorides, provided that the catalyst used for the reaction is a tri-substituted phosphine oxide or phosphine sulfide having the formula

(1)

wherein X means an oxygen atom or a sulfur atom, R1 and $R_2$ represent an aliphatic radical having up to 20 carbon atoms, preferably a lower alkyl radical having up to 6 carbon atoms, or a phenyl radical which may be substituted, or $R_1$ and $R_2$ jointly represent an alkylene radical being possibly unsaturated or substituted and having from 4 to 5 carbon atoms, and $R_3$ represents an aliphatic radical having up to 20 carbon atoms which may be unsaturated and/or substituted by halogen, hydroxy groups, alkoxy groups, acyloxy groups, nittrilo groups or, optionally, by substituted aryl groups or aryloxy groups, or $R_3$ represents a possibly substituted phenyl radical. Said catalyst may also be a reaction product obtained from compounds having formula 1 with phosgene and/or acids or acid anhydrides, or a mixture of these compounds. The catalyst is used in quantities of from 0.01 to 10 weight percent, preferably from 0.05 to 2 wt.% and particularly from 0.1 to 0.2 wt.%, calculated on the carboxylic acid or the carboxylic acid anhydride.

As far as the catalytic activity of the compounds of formula 1 is concerned, the nature and constitution of the substituents $R_1$, $R_2$ and $R_3$ are not critical. However, absolutely decivise is the triple substitution by organic radicals of the phosphine oxides or sulfides according to formula 1. The following catalysts — for example — may be used according to the inventions:

trimethyl-phosphine oxide
dimethyl-hexyl-phosphine oxide
dimethyl-octyl-phosphine oxide
dimethyl-dodecyl-phosphine oxide
dimethyl-eicosyl-phosphine oxide
dimethyl-hydroxymethyl-phosphine oxide
dimethyl-chloromethyl-phosphine oxide
dimethyl-(3-chloro-propyl)-phosphine oxide
dimethyl-benzyl-phosphine oxide
dimethyl-phenoxymethyl-phosphine oxide
dimethyl-(2,4,5-trichloro-phenoxymethyl)-phosphine oxide
dimethyl-phenyl-phosphine oxide
diethyl-dodecyl-phosphine oxide
dihexyl-dodecyl-phosphine oxide
trieicosyl-phosphine oxide
trichloropropyl-phosphine oxide
triphenyl-phosphine oxide
trimethyl-phosphine sulfide
dimethyl-phenyl-phosphine sulfide
P-methyl-phospholene-(3,4)-P-oxide Catalysts preferred are those having formula 1 containing as radicals $R_1$ and $R_2$, possibly substituted alkyl groups having up to 6 carbon atoms and as radical $R_3$ a possibly substituted aliphatic radical having up to 20 carbon atoms or a possibly substituted aromatic radical.

The trisubstituted phosphine oxides or phosphine sulfides of formula 1 may be replaced — in corresponding quantities and with identical catalytic action—by their reaction products with phosgene or their adducts with acids. These compounds are obtained, for example, upon blending substances of formula 1 with phosgene or acids, as in the phosgenation batch.

For a complete phosgenation reaction according to the invention it is often sufficient to use the catalysts in quantities of 0.01 wt.%, calculated on the carboxylic acid or the carboxylic acid anhydride used, preferably from 0.05 to 2 wt.%. But the use of larger catalyst portions, e.g. from 5 to 10 wt.%, yields very pure carboxylic acid chlorides, increasing catalyst quantities bringing about higher reaction speeds.

The temperatures at which the process of the invention is performed are partially determined by the qualities of the carboxylic acids or the carboxylic acid anhydrides used and range approximately from 0° to 180°C, preferably from 60° to 130°C.

By the phosgenation process according to the invention aliphatic, cycloaliphatic or araliphatic mono-functional or polyfunctional carboxylic acid or their anhydrides can be converted in good yields into the corresponding acid chlorides. One of the special advantages of this processing method is that even upon reacting the aromatic carboxylic acids or their anhydrides which are considerably more difficult to phosgenate, the results are excellent in respect to yield and quality of the product. The following examples represent carboxylic acids or their anhydrides appropriate for the phosgenation according to the invention: acetic acid, chloroacetic acid, propionic acid, butyric acid. 3,5,5-trimethyl-hexanoic acid, lauric acid, palmitic acid, stearic acid, cyclohexane-carboxylic acid, cyclohexane-1,4-dicarboxylic acid, benzoic acid, tolylic acids, chlorobenzoic acids, chloromethylbenzoic acids, nitrobenzoic acids, chloronitrobenzoic acids, 3,4,5-trimethoxy-benzoic acid, 4-carbomethoxy-benzoic acid, phthalic acid, isophthalic acid, terephthalic acid, trimellitic acid and naphthalene-carboxylic acids. Upon phosgenation of $\alpha/\beta$-unsaturated carboxylic acids such as acrylic acid, methacrylic acid or crotonic acid there are obtained $\alpha/\beta$-unsaturated carboxylic acid chlorides or, in case that hydrogen chloride is added, $\beta$-chloro-carboxylic acid chlorides.

Generally, it is possible to react liquid or low melting carboxylic acids or carboxylic acid anhydrides without additionally using solvents. Solid substances are expediently reacted above their melting temperature. But the phosgenation of the carboxylic acid component may also be performed in solution or in suspension, e.g. in the liquid chloride already present or in an inert solvent or a suspension agent; the most suitable proved to be the solvents generally used for phosgenation reactions, such as benzene, toluene, chlorobenzene, dichlorobenzene, ethyl acetate and butyl acetate.

The process according to the invention can be carried out either discontinuously or also continuously in known phosgenation apparatus. A suitable processing method consists, for example, of passing phosgene at reaction conditions through or over the reaction mixture containing the carboxylic acid component and the catalyst until the development of $CO_2$ and HCl going on simultaneously with the formation of carboxylic acid chloride is terminated and no more phosgene is consumed. The carboxylic acid chloride can be removed from the reaction mixture in ususal manner, e.g. by distillation or crystallization. However, since the process according to the invention yields particularly pure products, it is also possible to process the carboxylic acid chloride directly without any intermediate purifying operations immediately after having eliminated the excess phosgene and the hydrogen chloride.

The presence of small quantities of water in the reaction batch is not critical and does not impede the phosgenation reaction.

The catalysts according to the invention may be used once or several times without losing their original efficiency. After completion of the phosgenation, the carboxylic acid chloride formed may be e.g. distilled and the catalyst-containing distillation residue may be re-used for the phosgenation catalysis. Also, in the continuous process either fresh catalyst is added to the reaction mixture or, as well, the carboxylic acid chloride formed is eliminated by distillation and the catalyst still present in the residue is re-cycled into the phosgenation reaction. In the latter case possible catalyst losses should be compensated.

The following examples illustrate the invention:

EXAMPLE 1

In a flask being equipped with thermometer, agitator, gas inlet tube and reflux condenser, 100 g of 3,5,5-trimethylhexanoic-acid are heated to 80°C after having added 0.01 g of trimethylphosphine oxide; at this temperature phosgene is fed in until it is no longer consumed. A strong phosgene reflux then starts in the condenser adjusted to −20°C and the temperature of the contents of the flask is slipping slightly. In such a way there are introduced abt. 150 g of phosgene within a lapse of 4 hours. The reaction is continued for another approx. 1 hour, then the reflux condenser is removed so that the larger portion of the phosgene still in solution may escape as a gas. The rest is eliminated by blowing through nitrogen. Thus, a practically 100% yield of an almost colorless 3,5,5-trimethylhexanoic acid chloroide is obtained which contains as impurity less than 0.1% of the corresponding carboxylic anhydride and which is ready for further processing without any additional purifying manipulations.

COMPARATIVE TEST

If instead of the trimethyl phosphine oxide 0.02 g of tetramethylthio-urea is used as catalyst, the content in carboxylic anhydride after 8 hours of reaction time is still approx. 2%. Upon using 1 g of tetramethyl-ammonium chloride as catalyst this content rate is still greater than 25% after a 4-hour-reaction time. In these latter cases the anhydride-portion may be diminished by an additional distillation only.

EXAMPLE 2

According to the method described for example 1, 100 g of stearic acid are reacted with phosgene while adding 0.01 g of dimethyldodecyl-phosphine oxide. After a reaction time of abt, 6 hours a practically 100% yield of a product of approx. 98% purity is obtained which may be submitted for purification purposes to an additional distillation, if necessary.

EXAMPLE 3

In the device described for example 1, 122 g of benzoic acid are reacted with phosgene after having added 0.1 g of dimethyl-chloromethyl-phosphine oxide. At the beginning the operation is carried out at a temperature just above the melting point of the benzoic acid (122°C), but while the reaction is continuing the temperature is brought down to approx. 100°C. So as to avoid sublimation, it is useful to add to the reation mixture approx. 20 g of chlorobenzene. The phosgene absorption is terminated after abt. 2 hours. After a postreaction of another hour a more then 99% crude yield of a slightly colored benzoyl chloride is obtained which, for further purification, may be submitted to further distillation under reduced pressure. The net yield is abt. 136 g corresponding to 97% theoretical yield.

EXAMPLE 4

A mixture of 100 g of 3,4,5-trimethoxybenzoic acid, 150 g of xylene and 0.1 g of dimethyl-dodecyl-phosphine oxide is treated with phosgene at 100°C in the apparatus described for example 1. After a lapse of abt. 1 hour and phosgene consumption of 140 g the absorption of phosgene is terminated. At the end of a two-hours-postreaction a yellow solution of 3,4,5-trimethoxy-benzoylchloride is obtained. The yield in dissolved acid chloride is approx. 106 g, corresponding to 97.5% of the theoretical yield, calculated on the acid used. The solution may be used directly for further reactions after having eliminated the remaining phosgene by means of nitrogen or by distillation of a part of the solvent. But it is also possible to isolate the trimethoxy-benzoylchloride in its pure form by means of vacuum distillation (boiling point: 137°C/1.5 torr. softening point: 80 to 81°C).

COMPARATIVE TEST

If the aforesaid catalyst is replaced by 0.1 g of tetramethylthio urea, a dark-colored reaction solution, containing resinous fractions is obtained after a reaction period of 4 hours. When using 2.5 g of tetramethyl-ammonium chloride the phosgene absorption after 8 hours is 115 g, the yield in acid chloride is 90% of the theoretical yield.

EXAMPLE 5

A mixture of 90 g of terephthalic acid monomethyl ester, 100 g of chlorobenzene and 0.2 g of trimethyl-phosphine oxide is treated with phosgene according to example 4. The reaction is terminated after abt. 40 minutes.

A slightly yellow reaction solution having a content of 94 g of 4-carbomethoxy-benzoyl chloride is obtained corresponding to a theoretical yield of 94.7 %. A perfectly colorless acid chloride is obtained by vacuum distillation in a yield of 90% of the theoretical (boiling point=105°C /0.7 torr).

EXAMPLE 6

100 g of terephthalic acid are mixed, while agitating, with 150 g of chlorobenzene and treated with phosgene at 100°C after having added 0.1 g of trimethylphosphine oxide.

The phosgene absorption is terminated after 3 to 4 hours and after having introduced approx. 260 g of phosgene. Roughly half of this quantity of phosgene escapes into the waste gas together with $CO_2$ and HCl and may be condensed in a deep temperature condenser. After a postagitation period of approx. 1 hour the hardly colored, limpid reaction solution is distilled under reduced pressure. The terephthalic acid dichloride having a boiling point of 136°C / 9 torr passes over as a colorless distillate crystallizing at 81.6°C. The yield is 97 to 98% of the theoretical.

COMPARATIVE TEST

If trimethyl-phosphine oxide is replaced as a catalyst by 1.0 g of tetramethyl urea or 1.0 g of tetramethylthio urea or 0.1 g, 1.0 g or 2.5 g of tetramethyl-ammonium chloride, the rate of phosgene absorption is very low even hours later. The analogous use of dimethyl formamide as catalyst yields heavily yellow-colored solutions and also yellow distillation products.

EXAMPLE 7 to 17

The examples specified in the following table are carried out according to example 6, the trimethylphosphine oxide being replaced in each specific case by the catalyst shown in column 2. The columns 3, 4 and 5 indicate the phosgenation temperature, the reaction time and the yield in terephthalic acid dichloride.

| Example No. | Catalyst | Temp. °C | react.-time (hours) | yield % of (theoretic.yd.) |
| --- | --- | --- | --- | --- |
| 7 | 0.1 g $(CH_3)_2(C_{12}H_{25})$ P = O | 100 | 3 | 97.4 |
| 8 | 1.0 g $(CH_3)_2(C_{12}H_{25})$ P = O | 90 | 2.5 | 95.5 |
| 9 | 0.5 g $(CH_3)_2(C_{20}H_{41})$ P = O | 100 | 3 | 98.3 |
| 10 | 0.1 g $(CH_3)_2(CH_2OH)$ P = O | 100 | 5 | 94.3 |
| 11 | 0.1 g $(CH_3)_2(C_3H_6Cl)$ P = O | 100 | 3 | 94.5 |
| 12 | 0.1 g $(CH_3)_2(CH_2$—O—(2,4-dichlorophenyl)$)$ P = O | 100 | 3 | 96.5 |
| 13 | 0.1 g $(CH_3)_2(C_6H_5)$ P = O | 100 | 3.5 | 95.0 |
| 14 | 0.1 g $(C_2H_5)_2(C_{12}H_{25})$ P = O | 100 | 7 | 94.0 |
| 15 | 1.0 g $(C_6H_5)_3$ P = O | 120 | 12.5 | 97.7 |
| 16 | 0.1 g $(CH_3)_3$ P = S | 100 | 4.5 | 96.5 |
| 17 | 0.1 g (1-methylphospholane 1-oxide) | 100 | 3.5 | 98.3 |

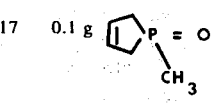

EXAMPLE 18

1.0 g of dimethyl-phenyl-phosphine sulfide are dissolved in 50 ml of benzene and treated with phosgene at 60°C. The reaction product of dimethyl-phenyl-phosphine sulfide with phosgene separates as colorless precipitate. The phosgene absorption terminated, the excess of phosgene and benzene is eliminated by distillation, towards the end under reduced pressure; 1.2 g of the reaction product of dimethyl-phenyl-phosphine sulfide and phosgene are obtained as an almost colorless, crystalline residue. To this residue are now added 100 g of terephthalic acid and 150 g of chlorobenzene. The mixture is phosgenated and worked up in analogy to example 6. Phosgenation time is abt. 1 hour, the yield in terephthalic acid dichloride is 93.2% of the theoretical.

EXAMPLE 19

A total quantity of 12,300 g of phosgene are introduced into a mixture of 8,479 g of acrylic acid and 127 g of trimethyl-phosphine sulfide, starting at room temperature. Simultaneously, the mixture is heated additionally up to the reaction temperature of 60°C. The heating source is then removed and the reaction temperature maintained at 60°C by increasing the quantity of phosgene introduced to approx. 800 g per hour and by cooling simultaneously. The end of the reaction is indicated by decrease of the reaction temperature. 13,800 g of β-chloropropionic acid chloride are obtained, boiling point 12 torr 43°C, equivalent to 92% of the theoretical yield. There remains a distillation residue of 1000 g of a crystal magma, approx. 13 wt.% of which consist of phosgenation catalyst. After having re-used same three times for further phosgenation operations there was no hint of its decreasing catalytic efficiency.

EXAMPLE 20

A fast current of 600 g of phosgene is introduced into a solution of 0.432 g of trimethylphosphine sulfide in 432 g of acrylic acid (stabilized with copper acetate), heated to 70°C. The subsequent distillation of the reaction mixture yields 278 g of acrylic acid chloride (boilg.pt. 200 torr 40°C) and 302 g of β-chloro-propionic acid chloride (boilg.pt. 12 torr 43°C).

EXAMPLE 21 to 27

If as per example 4 the carboxylic acid components according to column 2 of the following table are used instead of 3,4,5-trimethoxy benzoic acid, similarly good yields of the corresponding acid chlorides are obtained (see col.3):

| Ex. No. | carboxylic acid | yield carboxylic acid chloride % (theoretical yield) |
|---|---|---|
| 21 | 2-tolylic acid | 97.5 |
| 22 | 2-chloro-benzoic acid | 96.3 |
| 23 | 2,4-dichloro-benzoic acid | 94.7 |
| 24 | 4-nitro-benzoic acid | 94.3 |
| 25 | 3-nitro-4-chloro-benzoic acid | 93.8 |
| 26 | trimellitic acid | 92.0 (trimellitic acid trichloride) |
| 27 | trimellitic anhydride | 92.0 (trimellitic acid trichloride) |

What is claimed is:

1. A process for preparing a carboxylic acid chloride which comprises reacting a carboxylic acid or carboxylic acid anhydride with phosgene at a temperature from 0° to 180°C in the presence of 0.01 to 10 percent, by weight of said carboxylic acid or carboxylic acid anhydride, of a catalyst which is a trisubstituted phosphine oxide or phosphine sulfide of the formula

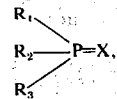

or is a reaction product thereof with at least one member selected from the group consisting of phosgene, said carboxylic acid, and said carboxylic acid anhydride, wherein X is oxygen or sulfur; $R_1$ and $R_2$, taken alone, are lower alkyl having up to 6 carbon atoms or phenyl; $R_1$ and $R_2$, taken together, are saturated or unsaturated alkylene having 4 to 5 carbon atoms; and $R_3$ is alkyl having up to 20 carbon atoms, haloalkyl, hydroxyalkyl, 2,4,6-trichlorophenoxy methyl, or phenyl.

2. The process defined in claim 1 wherein $R_1$ and $R_2$ are each lower alkyl having up to 6 carbon atoms.

3. The process defined in claim 1, wherein the catalyst is present in a concentration of from 0.05 to 2 weight percent.

4. The process defined in claim 3, wherein the catalyst is present in a concentration of from 0.1 to 0.2 weight percent.

5. The process defined in claim 1, wherein an inert solvent or suspension agent is added to the reaction mixture.

6. The process defined in claim 1, wherein the reaction takes place at a temperature of from 60° to 130°C.

7. The process according to claim 1, wherein the catalyst is recycled while operating continuously.

* * * * *